United States Patent
Xu et al.

(10) Patent No.: US 8,691,792 B2
(45) Date of Patent: Apr. 8, 2014

(54) METHODS AND COMPOSITIONS FOR IMPROVING GASTROINTETINAL HEALTH

(75) Inventors: Hui Xu, Chesterfield, MO (US); Dorothy Pauline LaFlamme, Floyd, VA (US); Carolyn Jean Cupp, Liberty, MO (US)

(73) Assignee: Nestec SA, Vevey (CH)

( * ) Notice: Subject to any disclaimer, the term of this patent is extended or adjusted under 35 U.S.C. 154(b) by 650 days.

(21) Appl. No.: 12/584,147

(22) Filed: Sep. 1, 2009

(65) Prior Publication Data

US 2011/0034411 A1    Feb. 10, 2011

Related U.S. Application Data

(60) Provisional application No. 61/273,506, filed on Aug. 5, 2009.

(51) Int. Cl.
*A01N 43/04*    (2006.01)
*A61K 31/715*   (2006.01)

(52) U.S. Cl.
USPC .......................................................... 514/54

(58) Field of Classification Search
None
See application file for complete search history.

(56) References Cited

U.S. PATENT DOCUMENTS 6,203,825 B1 *    3/2001   Hodgkins .................... 426/2
2005/0124576 A1 *  6/2005   Khoo et al. .................. 514/54

* cited by examiner

*Primary Examiner* — Layla Bland
(74) *Attorney, Agent, or Firm* — Julie M. Lappin; Robert M. Barrett

(57) ABSTRACT

Methods for maintaining or improving the gastrointestinal health of animals susceptible to or suffering from poor gastrointestinal health by administering to the animal a gastrointestinal health maintaining or improving amount of a food composition comprising from about 1 to about 20% carbohydrate; from about 3 to about 10% total dietary fiber, wherein the total dietary fiber contains from about 10 to about 40% soluble fiber and from about 90 to about 60% insoluble fiber; and from about 0.1 to about 10% omega-3 fatty acids; wherein the composition has a digestibility coefficient of at least 80. Generally, the compositions are administered to the animal to prevent or treat diarrhea or to improve stool quality. Further, the compositions may be administered in conjunction with one or more probiotics, prebiotics, anti-gastritis drugs, anti-enteritis drugs, or anti-diarrhea drugs, microbial exopolysaccharides, or combinations thereof to maintain or improve gastrointestinal health.

23 Claims, No Drawings

METHODS AND COMPOSITIONS FOR IMPROVING GASTROINTETINAL HEALTH

CROSS REFERENCE TO RELATED APPLICATIONS

This application claims priority to U.S. Provisional Application Ser. No. 61/273,506 filed Aug. 5, 2009, the disclosure of which is incorporated herein by this reference.

BACKGROUND OF THE INVENTION

1. Field of the Invention

The invention relates generally to methods and compositions for maintaining and improving gastrointestinal health and particularly to using novel food compositions for maintaining and improving gastrointestinal health.

2. Description of the Related Art

Animals need good gastrointestinal health for their ordinary well being but, unfortunately, poor gastrointestinal health is common. Poor gastrointestinal health can be quite serious and may require medical attention. Poor gastrointestinal health results from various causes that may produce diarrhea, poor stool quality, or other symptoms. Further, animals must efficiently and properly digest food to maintain good gastrointestinal health. However, poor gastrointestinal health interferes with the ordinary food digestion and adversely affects an animal's health and wellness.

Many gastrointestinal disorders are accompanied by diarrhea, a loose watery stool that can be extremely unpleasant to an animal or its caregiver. Many methods for combating diarrhea are known in the art. For example, US20070166295A1 discloses compositions for treating diarrhea in small domestic animals such as dogs and cats. The compositions contain kaolin, pectin, and probiotics. U.S. Pat. No. 5,516,798 discloses methods for treating diarrhea using methylamine. U.S. Pat. No. 5,576,001 discloses compositions for the treatment of diarrhea comprising carrots, rice, bananas and glucose in powdered form. U.S. Pat. No. 5,741,807 discloses using histidine for treating or preventing infectious and non-infectious diarrheas. U.S. Pat. No. 6,926,891 discloses the treatment of diarrhea with strains of *Bifidobacterium longum*. U.S. Pat. No. 6,835,376 discloses using *Lactobacillus paracasei* for preventing diarrhea caused by pathogenic bacteria. US20050260170A1 discloses using *Bifidobacteria* for preventing diarrhea caused by pathogenic bacteria. U.S. Pat. No. 6,998,119 discloses a feed composition containing *Bifidobacterium* bacteria capable of preventing diarrhea. US20070248582A1 discloses using lactic bacteria for the prevention of diarrhea. Similarly, poor stool quality is often indicative of milder forms of poor gastrointestinal health that do not result in diarrhea.

Current methods for maintaining and improving gastrointestinal health often involve modifying the diet, administering various foods thought to effect gastrointestinal health, or administering various drugs thought to be useful for maintaining or improving gastrointestinal health. These methods, while useful, have not solved the problem. There is, therefore, a need for new methods and compositions for maintaining and improving gastrointestinal health in an animal.

SUMMARY OF THE INVENTION

It is, therefore, an object of the invention to provide methods and compositions useful for maintaining or improving gastrointestinal health.

It is another object of the invention to provide methods and compositions useful for preventing or treating diarrhea.

It is a further object of the invention to provide methods and compositions useful for improving stool quality.

It is another object of the invention to provide methods and compositions useful for promoting the health and wellness of an animal.

It is another object of the invention to provide methods for providing optional nutrition for an animal with a compromised intestinal tract.

These and other objects are achieved using novel methods and compositions for improving gastrointestinal health in an animal. The methods comprise administering to an animal susceptible to or suffering from poor gastrointestinal health a gastrointestinal health improving amount of a composition comprising from about 1 to about 20% carbohydrate; from about 3 to about 10% total dietary fiber, wherein the total dietary fiber contains from about 10 to about 40% soluble fiber and from about 90 to about 60% insoluble fiber; and from about 0.1 to about 10% omega-3 fatty acids, wherein the ratio of omega-6 to omega-3 fatty acids is from about 1:1 to about 15:1; wherein the composition has a digestibility coefficient of at least 80.

The compositions are surprisingly effective for maintaining or improving gastrointestinal health, particularly for preventing or treating diarrhea and for improving stool quality. The compositions can, therefore, be used to promote the health and wellness of the animal.

Other and further objects, features, and advantages of the invention will be readily apparent to those skilled in the art.

DETAILED DESCRIPTION OF THE INVENTION

Definitions

The term "animal" means any animal susceptible to or suffering from poor gastrointestinal health. An animal is "susceptible to" a disease or condition if the animal exhibits symptoms that indicate that the animal is likely to develop the condition or disease. An animal is "suffering from" a disease or condition if the animal exhibits symptoms that are indicative that the animal has developed the condition or disease.

The term "companion animal" means domesticated animals such as cats, dogs, rabbits, guinea pigs, ferrets, hamsters, mice, gerbils, horses, cows, goats, sheep, donkeys, pigs, and the like.

The term "in conjunction" means that one or more of the compositions or compounds (e.g., anti-diarrhea drugs) of the invention are administered to an animal (1) together in a food composition or (2) separately at the same or different frequency using the same or different administration routes at about the same time or periodically. "Periodically" means that the compositions, food compositions, and compounds are administered on a dosage schedule acceptable for a specific composition, food composition, and compound and that the food compositions are administered or fed to an animal routinely as appropriate for the particular animal. "About the same time" generally means that the compositions, composition components, anti-diarrhea drugs, and food compositions are administered at the same time or within about 72 hours of each other. In conjunction specifically includes administration schemes wherein gastrointestinal tract improving agents such as anti-diarrhea drugs are administered for a prescribed period and the compositions are administered indefinitely.

The term "single package" means that the components of a kit are physically associated in or with one or more containers and considered a unit for manufacture, distribution, sale, or use. Containers include, but are not limited to, cans, bags, boxes, bottles, shrink wrap packages, stapled or otherwise affixed components, or combinations thereof. A single package may be containers of individual food compositions physically associated such that they are considered a unit for manufacture, distribution, sale, or use.

The term "virtual package" means that the components of a kit are associated by directions on one or more physical or virtual kit components instructing the user how to obtain the other components, e.g., in a bag containing one component and directions instructing the user to go to a website, contact a recorded message, view a visual message, or contact a caregiver or instructor to obtain instructions on how to use the kit.

The term "health and/or wellness of an animal" means the complete physical, mental, and social well being of the animal, not merely the absence of disease or infirmity.

The term "anti-diarrhea drug" means any compound, composition (other than the compositions of the invention), or drug useful for preventing or treating diarrhea.

The term "anti-gastritis drug" means any compound, composition (other than the compositions of the invention), or drug useful for preventing or treating gastritis.

The term "anti-enteritis drug" means any compound, composition (other than the compositions of the invention), or drug useful for preventing or treating enteritis.

The term "fecal quality" is synonymous with the term "stool quality."

The Invention

In one aspect, the invention provides methods for maintaining or improving the gastrointestinal health of an animal susceptible to or suffering from poor gastrointestinal health. The methods comprise administering to the animal a gastrointestinal health maintaining or improving amount of a composition comprising from about 1 to about 20% carbohydrate; from about 3 to about 10% total dietary fiber, wherein the total dietary fiber contains from about 10 to about 40% soluble fiber and from about 90 to about 60% insoluble fiber; and from about 0.1 to about 10% omega-3 fatty acids, wherein the ratio of omega-6 to omega-3 fatty acids is from about 1:1 to about 15:1; wherein the composition has a digestibility coefficient of at least 80.

In one embodiment, the methods comprise maintaining or improving gastrointestinal health by preventing or treating diarrhea. In another, the methods comprise improving gastrointestinal health by improving stool quality. In a further embodiment, the methods comprise preventing or treating gastritis. In another, the methods comprise preventing or treating enteritis. In yet another embodiment, the methods comprise preventing or treating vomiting associated with poor gastrointestinal health.

In another aspect, the invention provides compositions suitable for maintaining or improving the gastrointestinal health of an animal. The compositions comprise from about 1 to about 20% carbohydrate; from about 3 to about 10% total dietary fiber, wherein the total dietary fiber contains from about 10 to about 40% soluble fiber and from about 90 to about 60% insoluble fiber; and from about 0.1 to about 10% omega-3 fatty acids; wherein the composition has a digestibility coefficient of at least 80.

The inventions are based upon the discovery that food compositions containing specific amounts of carbohydrate, dietary fiber (with certain amounts of insoluble and soluble fibers), omega-3 fatty acids (in proportion to omega-6 fatty acids), and a relatively high digestibility coefficient have a beneficial affect on gastrointestinal health, particularly by preventing to treating diarrhea or by favorably affecting fecal quality when consumed by an animal.

Any carbohydrate or carbohydrate source suitable for consumption by an animal can be used in the compositions. Such carbohydrate sources include whole grain, ground grain, grain components, flour of rice, wheat, corn, oats, millet, soy, barley, rye, sorghum, cotton seeds, canola seeds, rapeseed, flax seeds, linseeds, flour, potatoes, sweet potatoes, cassava, carrots, peas, or combinations thereof. In addition, glycogen contained in animal, fish, or poultry tissue can be a source of carbohydrate.

The compositions comprise carbohydrates in amounts of from about from about 1 to about 20%, preferably from about 2 to about 16%, most preferably from about 4 to about 12%.

Any soluble fiber suitable for consumption by an animal can be used in the composition of the invention. Such soluble fibers include gums such as guar, carrageenan, gum arabic, cassia, and alginate; pectins; oats; oat bran; oligosaccharides such as fructooligosaccharides, soy oligosaccharides, and inulin; lentils; kidney beans; pinto beans; white beans; chicory; psyllium, peas; potatoes; sweet potatoes; or combinations thereof. Preferred soluble fibers are inulin, psyllium, chicory, and oat bran.

Any insoluble fiber suitable for consumption by an animal can be used in the composition of the invention. Such insoluble fibers include soy fiber, soy hulls, beet pulp, pea fiber, corn bran, peanut hulls, citrus pulp, fruit pomace, wheat bran, cellulose, legume pea hulls, bean hulls, kidney beans, lentils, white beans, or combinations thereof. Preferred insoluble fibers are cellulose, pea fibers, oat fibers, peanut hulls, bean hulls, and soy hulls.

In various embodiments, a blend of fiber sources is used to assure an appropriate mix of both soluble and insoluble fibers.

The compositions comprise from about 3 to about 10% total dietary fiber, preferably from about 4 to about 8%, most preferably from about 5 to about 7%. The total dietary fiber comprises from about 10 to about 40% soluble fiber and from about 90 to about 60% insoluble fiber, preferably from about 12 to about 36% soluble fiber and from about 88 to about 64% insoluble fiber, most preferably from about 15 to about 35% soluble fiber and from about 85 to about 65% insoluble fiber.

Suitable amounts for each component in the composition will depend on a variety of factors such as the species of animal consuming the composition; the particular components included in the composition; the age, weight, general health, sex, and diet of the animal; the animal's consumption rate; the gastrointestinal health history of the animal; and the like.

The compositions have a digestibility coefficient of at least 80, preferably at least 85, most preferably at least 90.

The compositions are administered to the animal in any amount effective to maintain or improve gastrointestinal health or promote health or wellness. Typically, the compositions are fed to the animal as a food comprising the majority, if not all, of the animal's diet. The amount will depend on factors such as the size of the animal and the animal's dietary requirements. Skilled artisans can easily determine the amount of the compositions needed to affect gastrointestinal health and promote health or wellness.

The compositions are administered orally to an animal using any suitable form for oral administration, e.g., palatable food compositions.

The compositions may contain additional ingredients such as vitamins, minerals, fillers, palatability enhancers, binding agents, flavors, stabilizers, emulsifiers, sweeteners, colorants, buffers, salts, coatings, and the like known to skilled artisans. Stabilizers include substances that tend to increase the shelf life of the composition such as preservatives, synergists and sequestrants, packaging gases, stabilizers, emulsifiers, thickeners, gelling agents, and humectants. Examples of emulsifiers and/or thickening agents include gelatin, cellulose ethers, starch, starch esters, starch ethers, and modified starches. The amount of such additives in a composition typically is up to about 5% by weight.

In one embodiment, the compositions are formulated to provide "complete and balanced" nutrition for an animal, preferably a companion animal such as a dog or a cat, according to standards established by the Association of American Feed Control Officials (AAFCO). In another embodiment, the composition is a pet food composition, e.g., dry kibbles and wet food compositions.

In various embodiments, the methods of the invention further comprise administering the composition in conjunction with at least one of a gastrointestinal health improving agent such as probiotics, prebiotics, anti-gastritis drugs, anti-enteritis drugs, and anti-diarrhea drugs.

Probiotics are live microorganisms that have a beneficial effect in the prevention and treatment of specific medical conditions when ingested. Probiotics are believed to exert biological effects through a phenomenon known as colonization resistance. The probiotics facilitate a process whereby the indigenous anaerobic flora limits the concentration of potentially harmful (mostly aerobic) bacteria in the digestive tract. Other modes of action, such as supplying enzymes or influencing enzyme activity in the gastrointestinal tract, may also account for some of the other functions that have been attributed to probiotics. Prebiotics are nondigestible food ingredients that beneficially affect host health by selectively stimulating the growth and/or activity of bacteria in the colon. Prebiotics include fructooligosaccharides (FOS), xylooligosaccharides (XOS), galactooligosaccharides (GOS), and mannooligosaccharides (typically for non-human foods such as petfoods). The prebiotic, fructooligosaccharide (FOS) is found naturally in many foods such as wheat, onions, bananas, honey, garlic, and leeks. FOS can also be isolated from chicory root or synthesized enzymatically from sucrose. FOS fermentation in the colon results in a large number of physiologic effects including increasing the numbers of *bifidobacteria* in the colon, increasing calcium absorption, increasing fecal weight, shortening of gastrointestinal transit time, and possibly lowering blood lipid levels. The increase in *bifidobacteria* has been assumed to benefit human health by producing compounds to inhibit potential pathogens, by reducing blood ammonia levels, and by producing vitamins and digestive enzymes. Probiotic bacteria such as *Lactobacilli* or *Bifidobacteria* are believed to positively affect the immune response by improving the intestinal microbial balance leading to enhanced antibody production and phagocytic (devouring or killing) activity of white blood cells. *Bifidobacterium lactis* could be an effective probiotic dietary supplement for enhancing some aspects of cellular immunity in the elderly. Probiotics enhance systemic cellular immune responses and may be useful as a dietary supplement to boost natural immunity in otherwise healthy adults. Probiotics include many types of bacteria and other microorganisms but generally are specific species and subspecies, e.g., *Enterococcus faecium* SF68, selected from limited genera of bacteria and other microorganisms: *Lactobacilllus, Bifidobacteria, Lactococcus, Pediococcus, Enterococcus* and *Saccharomyces*. The amount of probiotics and prebiotics to be administered to the animal is determined by the skilled artisan based upon the type and nature of the prebiotic and probiotic and the type and nature of the animal, e.g., the age, weight, general health, sex, extent of microbial depletion, presence of harmful bacteria, and diet of the animal. Generally, probiotics are administered to the animal in amounts of from about one to about twenty billion colony forming units (CFUs) per day for the healthy maintenance of intestinal microflora, preferably from about 5 billion to about 10 billion live bacteria per day. Generally, prebiotics are administered in amounts sufficient to positively stimulate the healthy microflora in the gut and cause these "good" bacteria to reproduce. Typical amounts are from about one to about 10 grams per serving or from about 5 to about 40% of the recommended daily dietary fiber for an animal. The probiotics and prebiotics can be made part of the composition by any suitable means. Generally, the agents are mixed with the composition or applied to the surface of the composition, e.g., by sprinkling or spraying. When the agents are part of a kit, the agents can be admixed with other materials or in their own package.

Anti-gastritis drugs useful in the invention are any anti-diarrhea drugs known to skilled artisans to be useful for combating gastritis, e.g., antacids; acid blockers; antibiotics; proton pump inhibitors such as omeprazole, lansoprazole, rabeprazole, and esomeprazole; and the like.

Anti-enteritis drugs useful in the invention are any anti-diarrhea drugs known to skilled artisans to be useful for combating enteritis, e.g., antibiotics, anti-diarrhea drugs, and the like.

Anti-diarrhea drugs useful in the invention are any anti-diarrhea drugs known to skilled artisans to be useful for combating diarrhea, e.g., loperamide, diphenoxylate, pancreatic lipase, and tincture of opium. Holistic anti-diarrhea drugs and compositions are also included in the invention, e.g., peppermint and ginger. The anti-diarrhea drugs are administered to the animal using any method appropriate for the anti-diarrhea drug and in amounts known to skilled artisans to be sufficient to prevent or treat diarrhea. The anti-diarrhea drugs have a beneficial effect on the gastrointestinal tract by reducing the incidence or severity of diarrhea.

In a further embodiment, the methods of the invention further comprise administering the compositions in conjunction with at least one microbial exopolysaccharide.

The microbial exopolysaccharides useful in the invention are any microbial exopolysaccharides capable of preventing or treating diarrhea. Examples of suitable microbial exopolysaccharides for use in the invention generally include those microbial exopolysaccharides synthesized from bacteria selected from the group consisting of *Sphingomonas paucimobilis, Agrobacterium biovar, Xanthomonas campestris, Alcaligenes* species*, Aureobasidium pullulans, Acetobacter xylinum, Sclerotium rolfsii, Schizophyllum commune, Saccharomyces cerevisiae* and *Sclerotium glucanicum*. In some embodiments, the microbial exopolysaccharide is selected from the group consisting of rhamsan, curdlan, xanthan gum, scleroglucan, PS-10 gum, PS-21 gum, PS-53 gum, polysaccharides from Alcaligenes species, PS-7 gum, gellan gum, curdlan, bacterial alginate, dextran, pullulan, baker's yeast glycan, bacterial cellulose, 6-deoxy-hexose-containing polysaccharides, and combinations thereof.

In a preferred embodiment, the microbial exopolysaccharide comprises a gellan gum. Gellan gum is a linear polysaccharide made from fermentation by *Sphingomonas paucimobilis* (elodea) (ATCC31461). Industrial preparation of the gum can be carried out by inoculating *Sphingomonas paucimobilis* into a fermentation broth containing glucose, glucuronic acid and rhamnose to form a tetrasaccharide repeating unit in a ratio of 2:1:1. In its native form, gellan gum is highly acylated with 1.5 acylgroup, acetyl and glycerate, per repeating unit. Modifications of the acyl groups both in number and type can be made as long as the basic anti diarrhea activity of the gellan gum is not significantly diminished. These different forms can be obtained from CP Kelco under different trade names including Gelrite®, K9A50 and other Kelco gellan gums including, but not limited to, Kelcogel LT®, Kelcogel F, and Kelcogel LT100®. As used throughout the specifications, "gellan" refers to the natural gum or acyl modified gum as long as the anti-diarrhea function is maintained.

Generally, the microbial exopolysaccharide is administered in amounts of from about 0.05 to about 2 g/kg/day. The amount of microbial exopolysaccharide in a particular composition can be adjusted by the skilled artisan based upon the amount of the composition the animal is to consume in a day.

The compositions can be administered in conjunction in various combinations of probiotics, prebiotics, anti-gastritis drugs, anti-enteritis drugs, anti-diarrhea drugs, and microbial exopolysaccharides. For example, the compositions can be administered in conjunction with a prebiotic to maintain gastrointestinal health. Similarly, the compositions can be administered in conjunction with a probiotic and an anti-diarrhea drug to treat diarrhea and improve gastrointestinal health. Likewise, the compositions can be administered in conjunction with a probiotic, a prebiotic, and an anti-diarrhea drug to treat diarrhea and improve gastrointestinal health.

In various embodiments, the compositions further comprise at least one of a gastrointestinal health improving agent selected from the group consisting of probiotics, prebiotics, anti-gastritis drugs, anti-enteritis drugs, anti-diarrhea drugs, and microbial exopolysaccharides. The gastrointestinal improving agent is added to the compositions in amounts sufficient to maintain or improve gastrointestinal health, particularly in combination with the compositions of the invention.

In another aspect, the invention provides methods for promoting the health or wellness of an animal susceptible to or suffering from poor gastrointestinal health. The methods comprise administering to the animal a health or wellness promoting amount of a composition comprising from about 1 to about 20% carbohydrate; from about 3 to about 10% total dietary fiber, wherein the total dietary fiber contains from about 10 to about 40% soluble fiber and from about 90 to about 60% insoluble fiber; and from about 0.1 to about 10% omega-3 fatty acids, wherein the ratio of omega-6 to omega-3 fatty acids is from about 1:1 to about 15:1; wherein the composition has a digestibility coefficient of at least 80.

The compositions promote the health or wellness of the animals and prevent or treat conditions that result in poor health or wellness of the animals, e.g., chronic diarrhea. The methods are useful for promoting the health or wellness of animals of any age or classification determined to be susceptible to or suffering from poor gastrointestinal health, including senior animals, geriatric animals, obese animals, overweight animals, and animals determined to be susceptible to or suffering from conditions that cause poor health or wellness in animals. The amount of the inventive compositions administered to the animal are the same amounts described herein for maintaining or improving the gastrointestinal health, typically a majority of an animal's diet.

Administration of the composition to an animal is useful for maintaining or improving the gastrointestinal health of the animal, particularly for preventing or treating diarrhea and for improving stool quality. Specifically, the administration of the composition to an animal has been shown to prevent diarrhea in an animal that has a tendency to have diarrhea from time to time and to reduce diarrhea in an animal already experiencing diarrhea. Similarly, the administration of the composition to an animal has been shown to improve stool quality in an animal that has poor gastrointestinal health that has not progressed to diarrhea.

The methods and compositions of the invention are useful for a variety of human and non-human animals susceptible to or suffering from poor gastrointestinal health, including avian, bovine, canine, equine, feline, hicrine, murine, ovine, and porcine animals. In some embodiments, the animal is a companion animal such as canine or feline, preferably a dog or a cat, most preferably a cat.

In another aspect, the invention provides packages comprising a material suitable for containing compositions of the invention and a label affixed to the package containing a word or words, picture, design, acronym, slogan, phrase, or other device, or combination thereof, that indicates that the contents of the package contains compositions useful for improving gastrointestinal health, particularly for preventing or treating diarrhea or for improving stool quality.

Typically, such device comprises the words "maintains gastrointestinal health," "promotes gastrointestinal health," "improves fecal quality," "reduces the severity and/or length of diarrhea," "promotes health and wellness," or an equivalent expression printed on the package. Any package or packaging material suitable for containing the composition is useful in the invention, e.g., bag, box, bottle, can, pouch, and the like manufactured from paper, plastic, foil, metal, and the like. In a preferred embodiment, the package contains a food composition adapted for a particular animal such as a human, canine, or feline, as appropriate for the label, preferably a companion animal food composition for dogs or cats.

In a further aspect, the invention provides kits suitable for maintaining or improving the gastrointestinal health of an animal susceptible to or suffering from poor gastrointestinal health. The kits comprise in separate containers in a single package or in separate containers in a virtual package, as appropriate, a composition of the invention and at least one of (1) one or more gastrointestinal tract improving agents; (2) one or more microbial exopolysaccharides; (3) instructions for how to combine the compositions and other kit components to maintain or improve gastrointestinal health, particularly to produce compositions useful for preventing or treating diarrhea or for improving stool quality; and (4) instructions for how to use the compositions and other kit components, particularly for the benefit of the animal.

In preferred embodiments, the gastrointestinal health improving agents are one or more of probiotics, prebiotics, anti-gastritis drugs, anti-enteritis drugs, and anti-diarrhea drugs.

When the kit comprises a virtual package, the kit is limited to instructions in a virtual environment in combination with one or more physical kit components. The kit contains the compositions and other components in amounts sufficient to maintain or improve gastrointestinal health. Typically, the compositions and the other suitable kit components are admixed just prior to consumption by an animal. In one embodiment, the kit contains a composition of the invention and a packet containing one or more compounds or materials beneficial to an animal's health when consumed by the animal. The kit may contain additional items such as a device for mixing the compositions and other kit components or a device for containing the admixture, e.g., a food bowl. In another embodiment, the compositions are mixed with additional nutritional supplements such as vitamins and minerals that promote good health in an animal.

In another aspect, the invention provides a means for communicating information about or instructions for one or more of (1) using the compositions of the invention for maintaining or improving gastrointestinal health; (2) using the compositions for improving stool quality; (3) using the compositions for preventing or treating diarrhea; (4) admixing the compositions with the other materials; (5) administering the compositions to an animal; (6) administering the compositions to an animal in combination with one or more gastrointestinal health improving agents; and (7) using the kits of the invention for maintaining or improving gastrointestinal health, particularly for preventing and treating diarrhea or for improving stool quality. The means comprises a document, digital storage media, optical storage media, audio presentation, or visual display containing the information or instructions. In certain embodiments, the communicating means comprises a document, digital storage media, optical storage media, audio presentation, or visual display containing the information or instructions. Preferably, the communication means is a displayed web site or a brochure, product label, package insert, advertisement, or visual display containing such information or instructions. Useful information includes one or more of (1) methods and techniques for combining and administering the compositions and/or other components and (2) contact information for animals or their caregivers to use if they have a question about the invention and its use. Useful instructions include amounts for mixing and administration amounts and frequency. The communication means is useful for instructing on the benefits of using the invention and communicating the approved methods for administering the invention to an animal.

In a further aspect, the invention provides a method for providing optional nutrition for an animal with a compromised intestinal tract comprising administering to the animal a composition comprising from about 1 to about 20% carbohydrate; from about 3 to about 10% total dietary fiber, wherein the total dietary fiber contains from about 10 to about 40% soluble fiber and from about 90 to about 60% insoluble fiber; and from about 0.1 to about 10% omega-3 fatty acids, wherein the ratio of omega-6 to omega-3 fatty acids is from about 1:1 to about 15:1; wherein the composition has a digestibility coefficient of at least 80.

All percentages expressed herein are by weight of the composition on "dry matter basis" unless specifically stated otherwise. The term "dry matter basis" means that an ingredient's percentage in a composition is measured after the moisture in the composition has been removed.

The dosages expressed herein are in grams per kilogram of body weight per day (g/kg/day) unless expressed otherwise.

The invention is not limited to the particular methodology, protocols, and reagents described herein because they may vary. Further, the terminology used herein is for the purpose of describing particular embodiments only and is not intended to limit the scope of the present invention.

As used herein, ranges are used herein in shorthand, so as to avoid having to list and describe each and every value within the range. Any appropriate value within the range can be selected, where appropriate, as the upper value, lower value, or the terminus of the range.

As used herein, the singular form of a word includes the plural, and vice versa, unless the context clearly dictates otherwise. Thus, the references "a", "an", and "the" are generally inclusive of the plurals of the respective terms. For example, reference to "a composition" or "a method" includes a plurality of such "composition" or "method." Similarly, the words "comprise", "comprises", and "comprising" are to be interpreted inclusively rather than exclusively. Likewise the terms "include", "including" and "or" should all be construed to be inclusive, unless such a construction is clearly prohibited from the context. Similarly, the term "examples," particularly when followed by a listing of terms, is merely exemplary and illustrative and should not be deemed to be exclusive or comprehensive.

Unless defined otherwise, all technical and scientific terms and any acronyms used herein have the same meanings as commonly understood by one of ordinary skill in the art in the field of the invention. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, and other references cited or referred to herein are incorporated herein by reference to the extent allowed by law. The discussion of those references is intended merely to summarize the assertions made therein. No admission is made that any such patents, patent applications, publications or references, or any portion thereof, are relevant prior art for the present invention and the right to challenge the accuracy and pertinence of such patents, patent applications, publications, and other references is specifically reserved.

EXAMPLES

The invention can be further illustrated by the following examples, although it will be understood that these examples are included merely for purposes of illustration and are not intended to limit the scope of the invention unless otherwise specifically indicated.

The following food compositions were used in the Examples:

| Food Composition A | | |
|---|---|---|
| Ingredient | % As Fed | % Dry Matter |
| Moisture | 76.95 | |
| Protein | 8.925 | 38.72 |
| Fat | 6.03 | 26.16 |
| Carbohydrates | 6.303 | 27.34 |
| Insoluble Fiber | 2.42 | 10.50 |
| Soluble Fiber | 0.54 | 2.34 |
| Total Dietary Fibers | 2.92 | 12.67 |
| C20:5n3 Eicosapentaenoic Acid | ND* | ND |
| Total Omega-3 fatty acids | 0.08 | 0.37 |
| Total Omega-6 fatty acids | 1.56 | 6.75 |

*Not Detectable

| Food Composition B | | |
|---|---|---|
| Ingredient | % As Fed | % Dry Matter |
| Moisture | 76.4 | |
| Protein | 11.6 | 49.15 |
| Fat | 6.64 | 28.14 |
| Carbohydrates | 2.986 | 12.65 |
| Insoluble Fiber | 1.34 | 5.68 |
| Soluble Fiber | 0.3 | 1.27 |
| Total Dietary Fibers | 1.64 | 6.95 |
| C20:5n3 Eicosapentaenoic Acid | 0.09 | 0.40 |
| Total Omega-3 fatty acids | 0.24 | 1.01 |
| Total Omega-6 fatty acids | 1.15 | 4.87 |

The following method was used to evaluate stool quality. Stool quality was determined using a fecal scoring system with scores between 1 and 7. Normal stools are scored as a 2 or 3. A description of each score is:

Score 1—very hard and dry, requires much effort to expel from body;
Score 2—firm, but not hard; should be pliable; segmented appearance; little or no residues left on ground when picked up;
Score 3—Log-like, little or no segmentation visible; moist surface, leaves residues, but hold form when picked up;
Score 4—very moist (soggy), distinct log shape visible; leaves residues and loses form when picked up;
Score 5—very moist but has distinct shape; present in piles rather than as distinct logs; leaves residue and loses form when picked up;
Score 6—Has texture, but no defined shape; occurs as a pile or as spots; leaves residue when picked up; and
Score 7—Watery, no texture, flat; occurs as puddles.

Diarrhea is generally defined as either excessively watery feces, increased stool volume, or both. However, the threshold is not always well defined. As a general rule, a fecal score of 5 or greater on the 7 point scale is suggestive of diarrhea. Poor stool quality is indicated by a score of 4 or greater.

Example 1

Sixteen (16) cats with naturally occurring diarrhea were fed a commercially available canned food composition to standardize the cat's diet ("Baseline"). Then, the cats were divided into two (2) groups and fed either Food Composition A (FCA) or Food Composition B (FCB) for 4 weeks (Phase 1). During the last week of the Phase 1, diarrhea was assessed via fecal scoring, where 7=very watery; 2 to 3 is optimum; 1 is very hard and dry. Then, cats that had been fed FCA were then switched to FCB and cats that had been fed FCB were switched to FCA for another 4 weeks (Phase 2), during the last week of the Phase 2, fecal scoring was repeated. The results are shown in Table 1.

Referring to Table 1, cats FCB had significantly greater improvement in fecal score, compared to those FCA. Other data show that for cats fed FCA, only 12.5% of cats developed normal stools. In contrast, 43.8% of cats fed FCB developed normal stools (defined as a fecal score of 2 or 3).

TABLE 1

| | | Fecal Scores | | | |
|---|---|---|---|---|---|
| Time | Group | Product | N | Mean | Std. Error |
| Baseline | 1 | Control | 9 | 5.7972 | 0.4771 |
| Phase 1 | 1 | Diet A | 9 | 4.8656 | 0.4771 |
| Phase 2 | 1 | Diet B | 9 | 3.8806 | 0.4771 |
| Baseline | 2 | Control | 7 | 5.0873 | 0.541 |
| Phase 1 | 2 | Diet B | 7 | 3.6489 | 0.541 |
| Phase 2 | 2 | Diet A | 6 | 4.199 | 0.5576 |

Example 2

Fifteen (15) cats with naturally occurring diarrhea or poor stool quality were fed FCB for 4 weeks after which diarrhea was assessed using fecal scoring, where 7=very watery; 2 to 3 is optimum; 1 is very hard and dry. The results are shown in Table 2.

Referring to Table 2, the data shows that there was a significant reduction in diarrhea, with average fecal scores improving (getting smaller), on average, by greater than 1 unit. Over 45% of cats with chronic diarrhea improved with diet alone when fed FCB. The data also shows that animals fed FCB had improved stool quality.

TABLE 2

| | Fecal Scores | | | | |
|---|---|---|---|---|---|
| | N | Week | Mean | Std Dev | P value |
| Baseline | 15 | 0 | 4.84582 | 1.202621 | |
| Diet B | 15 | 4 | 3.683519 | 1.691613 | |
| Mean change | 15 | | 1.162302 | 1.136371 | 0.0014 |

In the specification, there have been disclosed typical preferred embodiments of the invention. Although specific terms are employed, they are used in a generic and descriptive sense only and not for purposes of limitation. The scope of the invention is set forth in the claims. Obviously many modifications and variations of the invention are possible in light of the above teachings. It is therefore to be understood that within the scope of the appended claims, the invention may be practiced otherwise than as specifically described.

What is claimed is:

1. A method for maintaining or improving the gastrointestinal health of a feline susceptible to or suffering from poor gastrointestinal health comprising administering to the animal a gastrointestinal health maintaining or improving amount of a composition comprising from about 1 to about 20% carbohydrate; from about 3 to about 10% total dietary fiber, wherein the total dietary fiber contains from about 10 to about 40% soluble fiber comprising at least one of psyllium or oat bran and from about 90 to about 60% insoluble fiber comprising a compound selected from the group consisting of pea fibers, oat fibers, bean hulls, and combinations thereof, the carbohydrates comprising the soluble fiber and the insoluble fiber; and from about 0.1 to about 10% omega-3 fatty acids; wherein the composition has a digestibility coefficient of at least 80.

2. The method of claim 1 wherein maintaining or improving gastrointestinal health comprises preventing or treating diarrhea.

3. The method of claim 2 wherein the diarrhea is chronic.

4. The method of claim 1 wherein improving gastrointestinal health comprises improving stool quality.

5. The method of claim 1 wherein maintaining or improving gastrointestinal health comprises preventing or treating gastritis.

6. The method of claim 1 wherein maintaining or improving gastrointestinal health comprises preventing or treating enteritis.

7. The method of claim 1 wherein maintaining or improving gastrointestinal health comprises preventing or treating vomiting.

8. The method of claim 1 further comprising administering the composition in conjunction with at least one microbial exopolysaccharide.

9. The method of claim 8 wherein the microbial exopolysaccharide is selected from the group consisting of rhamsan, curdlan, xanthan gum, scleroglucan, PS-10 gum, PS-21 gum, PS-53 gum, polysaccharides from Alcaligenes species, PS-7 gum, gellan gum, curdlan, bacterial alginate, dextran, pullulan, baker's yeast glycan, bacterial cellulose, 6-deoxy-hexose-containing polysaccharides, and combinations thereof.

10. The method of claim 8 wherein the microbial exopolysaccharide is administered to the animal in amounts of from about 0.05 to about 2 g/kg/day.

11. A composition useful for maintaining or improving the gastrointestinal health of a feline comprising a gastrointestinal health maintaining or improving amount of a composition comprising from about 1 to about 20% carbohydrate; from about 3 to about 10% total dietary fiber, wherein the total dietary fiber contains from about 10 to about 40% soluble fiber comprising at least one of psyllium or oat bran and from about 90 to about 60% insoluble fiber comprising a compound selected from the group consisting of pea fibers, oat fibers, bean hulls, and combinations thereof, the carbohydrates comprising the soluble fiber and the insoluble fiber; and from about 0.1 to about 10% omega-3 fatty acids; wherein the composition has a digestibility coefficient of at least 80.

12. The composition of claim 11 further comprising at least one microbial exopolysaccharide.

13. The composition of claim 12 wherein the microbial exopolysaccharide is selected from the group consisting of rhamsan, curdlan, xanthan gum, scleroglucan, PS-10 gum, PS-21 gum, PS-53 gum, polysaccharides from Alcaligenes species, PS-7 gum, gellan gum, curdlan, bacterial alginate, dextran, pullulan, baker's yeast glycan, bacterial cellulose, 6-deoxy-hexose-containing polysaccharides, and combinations thereof.

14. The composition of claim 12 wherein the composition contains sufficient microbial exopolysaccharide to administer the microbial exopolysaccharide to the animal in amounts of from about 0.05 to about 2 g/kg/day.

15. A method for promoting the health or wellness of an animal comprising administering to an animal a health or wellness promoting amount of a composition comprising from about 1 to about 20% carbohydrate; from about 3 to about 10% total dietary fiber, wherein the total dietary fiber contains from about 10 to about 40% soluble fiber comprising at least one of psyllium or oat bran and from about 90 to about 60% insoluble fiber comprising a compound selected from the group consisting of pea fibers, oat fibers, bean hulls, and combinations thereof, the carbohydrates comprising the soluble fiber and the insoluble fiber; and from about 0.1 to about 10% omega-3 fatty acids, wherein the ratio of omega-6 to omega-3 fatty acids is from about 1:1 to about 15:1; wherein the composition has a digestibility coefficient of at least 80.

16. The method of claim 1 wherein the composition comprises from about 2 to about 16% carbohydrate.

17. The method of claim 1 wherein the composition comprises from about 4 to about 12% carbohydrate.

18. The method of claim 1 wherein the composition comprises from about 4 to about 8% total dietary fiber, wherein the total dietary fiber contains from about 12 to about 36% soluble fiber and from about 88 to about 64% insoluble fiber.

19. The method of claim 1 wherein the composition comprises from about 5 to about 7% total dietary fiber, wherein the total dietary fiber contains from about 15 to about 35% soluble fiber and from about 85 to about 65% insoluble fiber.

20. The composition of claim 11 comprising from about 2 to about 16% carbohydrate.

21. The composition of claim 11 comprising from about 4 to about 12% carbohydrate.

22. The composition of claim 11 comprising from about 4 to about 8% total dietary fiber, wherein the total dietary fiber contains from about 12 to about 36% soluble fiber and from about 88 to about 64% insoluble fiber.

23. The composition of claim 11 comprising from about 5 to about 7% total dietary fiber, wherein the total dietary fiber contains from about 15 to about 35% soluble fiber and from about 85 to about 65% insoluble fiber.

* * * * *

UNITED STATES PATENT AND TRADEMARK OFFICE
CERTIFICATE OF CORRECTION

PATENT NO. : 8,691,792 B2  
APPLICATION NO. : 12/584147  
DATED : April 8, 2014  
INVENTOR(S) : Xu et al.

Page 1 of 1

It is certified that error appears in the above-identified patent and that said Letters Patent is hereby corrected as shown below:

On the Title Page, Item (54) and in the Specification, Column 1, line 2, in the Title: "gastrointetinal" should read -- gastrointestinal --

In the Specification  
Column 4, line 2: "affect" should read -- effect --  
Column 4, line 10: "cassaya" should read -- cassava --  
Column 5, line 16: "and" should read -- or --  
Column 6, line 7: "live bacteria" should read -- CFUs of live bacteria --  
Column 8, line 38: "gastrointestinal tract improving" should read -- gastrointestinal tract health improving --

Signed and Sealed this  
Twenty-second Day of July, 2014

Michelle K. Lee  
*Deputy Director of the United States Patent and Trademark Office*